United States Patent [19]

Yatagai et al.

[11] Patent Number: 4,943,652

[45] Date of Patent: Jul. 24, 1990

[54] PROCESS FOR ASYMMETRICALLY REDUCING CARBONYL COMPOUNDS

[75] Inventors: Masanobu Yatagai; Takashi Ohnuki, both of Kawasaki, Japan

[73] Assignee: Ajinomoto Co., Inc., Tokyo, Japan

[21] Appl. No.: 270,514

[22] Filed: Nov. 14, 1988

[30] Foreign Application Priority Data

Nov. 11, 1987 [JP] Japan ................................ 62-284987
Apr. 19, 1988 [JP] Japan ................................ 63-95900

[51] Int. Cl.$^5$ .............................................. C07C 69/76
[52] U.S. Cl. ...................................... 560/60; 560/179; 549/295; 564/170; 568/812; 568/715; 568/814
[58] Field of Search ....................... 568/814, 812, 715; 560/60, 179; 549/295; 564/170

[56] References Cited

PUBLICATIONS

Chemical Abstracts vol. 101, #19 170757y, 1984.
*Chemical Abstracts,* vol. 101, p. 659, "Sodium Borohydride: Tartartic Acid. A Novel and Facile Reducing Agent For Cyclic Ketones" C. Adams.
*Houben-Weyl,* vol. 6/1B, pp. 90–1004, 257, "Methoden Der Organischen Chemie", T. Verlag.
*Journal of the Chemical Society,* (1981), pp. 900–905, "Asymmetric Reduction of Aromatic Ketones with Reagents Prepared From Sodium Borohydride and Various Carboxylic Acids in the Presence of 1,2:5,6-Di--O–Isopropylidene–Alpha–D–Glucofuranose", A. Hirao, et al.
*Journal of Organic Chemistry,* (1980), vol. 45, pp. 4231–4233, "Asymmetric Reduction of Prochiral Aromatic Ketones with Modified Reagents . . . " A. Hirao, et al.

*Primary Examiner*—Paul J. Killos
*Attorney, Agent, or Firm*—Oblon, Spivak, McClelland, Maier & Neustadt

[57] ABSTRACT

There is disclosed a process for asymmetrically reducing a carbonyl compound, which comprises reducing the carbonyl compound by the use of a reducing agent comprising (i) an optically active tartaric acid or ester thereof and (ii) a metal borohydride, thereby producing an optically active hydroxyl compound. The process can be used for the production of optically active hydroxyesters and alcohols from ketoesters and ketones. These products are useful for the production of medicaments and liquid crystals.

9 Claims, No Drawings

PROCESS FOR ASYMMETRICALLY REDUCING CARBONYL COMPOUNDS

FIELD OF THE INVENTION

The present invention relates to a novel process for the asymmetical reduction of carbonyl compounds such as ketoesters and ketones. More particularly, it relates to a process for producing optical active hydroxyesters or alcohols by the reduction of ketoesters or ketones.

The hydroxyesters and alcohols obtained by the process of the present invention are useful as intermediates for the production of medicaments, including β-lactam antibiotics of the 4th generation, such as carbapenems (e.g. thienamycin), as well as for the production of liquid crystals.

BACKGROUND OF THE INVENTION

Various processes have been proposed for the production of optical active hydroxyesters and alcohols including (1) asymmetric reduction processes utilizing yeasts ((a) B. S. Deol, D. D. Ridley and G. W. Simpson *Aust. J. Chem.* 29,2459 (1976), (b) D. Seebach and A. Fiechter, *Angew. Chem. Int. Ed. Engl.*, 23, 151 (1984), (c) H. Akita, A. Furuichi, H. Koshiji, K. Horikoshi and T. Oishi, *Tetrahedron Lett.*, 1982, 4051, (d) B. Zhou, A. S. Gopalan, F. Van-Middlesworth, W. R. Shieu and C. J. Sih, *J. Am. Chem. Soc.*, 105, 5925 (1983), and (e) K. Mori *Tetrahedron*, 37, 1341 (1981)); (2) reduction processes using modified Raney nickel catalysts ((a) M. Nakahata, M. Imaida, H. Ozaki, T. Harada and A. Tai, *Bull. Chem. Soc. Jpn.*, 55, 2186 (1982), and (b) T. Kikukawa, Y. Iizuka, T. Harada and A. Tai, *Chem. Lett.*, 1987, 1267); (3) reduction processes employing modified metal hydrides ((a) K. Soai, T. Yamazaki, H. Hikima and H. Oyamada, *J. Chem. Soc., Chem. Commum.*, 1985, 138, and (b) T. Mukaiyama, K. Tomimori and T. Oriyama, *Chem. Lett.*, 1985, 813); (4) reduction processes using asymmetric diphosphine-rhodium complexes ((a) K. Achiwa, *Tetrahedron lett.*, 1977, 3735, (b) I. Ojima, T. Kogure and K. Achiwa, *J. Chem. Soc., Chem. Commun.*, 1977, 428, and (c) I. Ojima, T. Kogure, T. Terasaki and K. Achiwa, *J. Org. Chem.*, 43, 3444 (1987)). However, these known processes suffer from difficulties in the preparation of reducing agents, low reaction temperature and/or poor chemical and optical yields, and therefore are not suited for commercial production of optical active hydroxyesters and alcohols.

SUMMARY OF THE INVENTION

It has been desired to develop a simple process that enables one to produce optical active hydroxyesters and alcohols in high yields and at low costs.

It is therefore an object of the present invention to provide a process for asymmetrically reducing carbonyl compounds by using readily available compounds.

It is another object of the present invention to provide a process for asymmetrically reducing carbonyl compounds such as ketoesters and ketones on a commercial scale to hydroxyl compounds such as hydroxyesters and alcohols by a simple reaction procedure at a relatively high temperature.

It is a further object of the present invention to provide a process for producing optical active hydroxyl compounds such as hydroxyesters and alcohols in high chemical and optical yields, by a simple reaction and a simple purification procedure.

According to the present invention, there is provided a process for asymmetrically reducing a carbonyl compound, which comprises reducing the carbonyl compound by the use of a reducing agent comprising (i) an optically active tartaric acid or ester thereof and (ii) a metal borohydride, thereby producing an optically active hydroxyl compound.

Thus, it has now been found that optical active hydroxyl compounds and as hydroxyesters and alcohols can be obtained in high yield and high purity by asymmetrically reducing carbonyl compounds such as ketoesters or ketones by the use of particular reducing agents as defined above. Preferably, the reducing agent, a reaction product of commercially available optical active tartaric acid or an ester thereof with a metal borohydride, e.g. sodium borohydride.

DESCRIPTION OF THE PREFERRED EMBODIMENTS

Preferred ketoesters to be used in the process of the present invention are linear or cyclic esters represented by Formula [I] and the reduction products resulting from the process in this case are linear or cyclic hydroxyesters represented by Formula [II]:

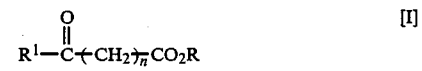

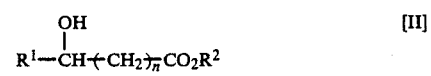

in which $R^1$ and $R^2$, which may be the same or different, each represents an alkyl group, an alkenyl group, an alkynyl group, an aryl group or an aralkyl group which may be substituted by one or more halogen atoms such a chlorine and bromine, or $R^1$ and $R^2$ may, individually or in combination, form a ring; and n represents an integer of from 1 to 3. Examples of alkyl, alkenyl, alkynyl and aryl groups are straight or branched, saturated or unsaturated, hydrocarbon groups having 1 to 12 carbon atoms which may be substituted by one or more halogen atoms (such as chlorine and bromine) and/or by other substituent groups such as amido, amino, alkoxy, nitrilo, ureido or nitro groups. Examples of aryl groups are phenyl, biphenyl and naphthyl groups, the phenyl rings of which may be substituted by one or more substituent groups such as halogen atoms, trifluoromethyl groups, lower alkyl groups containing 1 to 5 carbon atoms, or nitro, amino, alkoxy, nitrilo or ureido groups. By the term "aralkyl" is meant herein an alkyl group of 1 to 5 carbon atoms which may be substituted by one or more of the above-described aryl groups.

Preferred ketones for use in the present invention are linear or cyclic ketones represented by Formula [III] and containing a hetero atom or atoms on at least one of the α- and β-carbon atoms of at least one of the two substituent groups attached to the carbonyl group. The reduction products are linear or cyclic alcohols represented by Formula [IV] and containing a hereto atom or atoms on at least one of the α- and β-carbon atoms:

In the above formula [III] and [IV], X denotes a substituent group containing a hereto atom or atoms attached to at least one of the α- and β-carbon atoms. The hereto atom may be a nitrogen, oxygen, sulfur or halogen atom. X and Y may, individually or in combination, form a closed ring. Y denotes an alkyl group having 1 to 12 carbon atoms, an alkenyl group having 2 to 13 carbon atoms, an alkynyl group having 2 to 13 carbon atoms, an aryl group having 6 to 17 carbon atoms, or an aralkyl group having 7 to 18 carbon atoms.

The carbonyl compound is preferably reacted in an inactive medium with a reaction product of an optical active tartaric acid or an ester thereof and a metal borohydride or a metal borohydride-containing compound. The optical active tartaric acid or an ester thereof is preferably used in amount not less than 0.5 mol, more preferably in an amount of from 0.75 to 2.0 mol, per mol of borohydride. The configuration of the asymmetric carbon atom in the hydroxyl compound formed by the reduction depends upon the configuration of the tartaric acid or ester used. In other words, where L-(+)-tartaric acid is used, there are obtained hydroxyl compounds containing an asymmetric carbon having a configuration different from that of the hydroxyl compounds obtained where D-(−)-tartaric acid is used. Therefore, the configuration of the tartaric acid or ester should be selected in accordance with the desired configuration of the product.

The metal borohydride such as sodium borohydride is preferably used in an amount not less than 0.5 mol, more preferably in an amount of from 2 to 4 mol, per mol of carbonyl compound.

Any inactive medium which does not participate in the reaction can be used in the process of the invention. As examples of suitable inactive media, mention may be made of aromatic solvents such as benzene, toluene and xylene, and ethers such as diethyl ether, tetrahydrofuran (THF), dioxane and diglyme. These solvents can be used either individually or in combination.

To produce the optical active hydroxyl compound, the process of the invention is preferably carried out as follows. In the first place, the optical active tartaric acid or an ester thereof and the metal borohydride, are dispersed in an active medium and heated therein (first reaction). Thereafter, the temperature of the medium is lowered, and the carbonyl compound is added thereto so as to effect the reduction (second reaction). The first reaction is allowed to proceed at a temperature which is preferably in the range of from room temperature to the reflux temperature of the reaction mixture. The second reaction is allowed to proceed at a temperature which is preferably in the range of from −80° to 50° C., more preferably from −20° to 25° C.

After the disappearance of the carbonyl compound has been confirmed, the reaction can be terminated by the addition of, for example, 1N hydrochloric acid, and the reaction product is subjected to an appropriate aftertreatment and purification to give an optical active hydroxyl compound. Crude reaction products obtained can be purified in accordance with any conventional purification method, for example, column chromatography, recrystallization, distillation, or the like.

The process of the present invention allows the asymmetrical reduction of ketoesters and ketones by the use of a commercially available optical active tartaric acid or an ester thereof as reducing agent. Thus, optical active hydroxyesters and alcohols can be efficiently prepared by simple operations from corresponding ketoesters and ketones. Hence, the present invention is of great industrial use.

EXAMPLES

The present invention will now be illustrated by way of Examples.

In the Examples, the specific rotations of the hydroxyl compounds obtained were measured and compared with those of standard substances with a known purity, and their optical yield was calculated by the following equation:

$$\text{Optical Yield (\%)} = \frac{\text{Specific Rotation of Reduction Product}}{\text{Specific Rotation of Standard Substance} \times \text{Optical Purity of Standard Substance}}$$

The structure of the hydroxyl compounds obtained was confirmed by nuclear magnetic resonance ($^1$H NMR).

EXAMPLE 1

To a dispersion of 1.16 g (30 mmol) of sodium borohyride in 95 ml of THF, there was added 4.60 g (30.4 mmol) of L-(+)-tartaric acid, and the resulting mixture was stirred under reflux for 8 hours in an oil bath at 70° C. The reaction mixture was cooled in a cryostat at −20° C., and a solution of 1 g (7.6 mmol) of ethyl acetoacetate in 5 ml of THF was added dropwise with stirring to the mixture over a period of 10 minutes. The mixture was stirred for an additional 17 hours, and mixed with 50 ml of ethyl acetate and then with 40 ml of 1N hydrochloric acid, during which the mixture was cooled in an ice-water bath. After being stirred for an additional 15 minutes with cooling, the organic layer was separated. The aqueous layer was extracted with 20 ml of ethyl acetate, and the combined organic layers were washed twice with saturated aqueous sodium hydrogen carbonate (30 ml each time) and then with 50 ml of saturated aqueous sodium chloride, and were thereafter dried with anhydrous magnesium sulfate. After the solvent had been removed under reduced pressure, the residue was purified by silica gel column chromatography, using a mixture of ethyl acetate and n-hexane (1:5) as an eluent. There was obtained 0.66 g of the ethyl ester of (R)-(−)-hydroxybutanoic acid, having a specific rotation [α] $D^{20}$ of −35.1° (cl. 28, CHCl$_3$). The synthesis yield was 65% and the optical yield was 81% (see Reference 1).

EXAMPLE 2

To a dispersion of 0.96 g (25.2 mmol) of sodium borohydride in 80 ml of THF, there were added 3.81 g (25.2 mmol) of L-(+)-tartaric acid, and the resulting mixture was stirred under reflux for 4 hours in an oil bath at 70° C. The reaction mixture was cooled in a cryostat at −20° C., and a solution of 1 g (6.3 mmol) of n-butyl acetoacetate in 5 ml of THF was added dropwise with stirring to the mixture over a period of 10 minutes. The mixture was stirred for an additional 24 hours under the same conditions. After the completion of the reaction, the reaction mixture was subjected to a treatment as described in Example 1 to give 0.89 g of the n-butyl ester of (R)-(−)-3-hydroxybutanoic acid, having a specific rotation $[\alpha]_D^{20}$ of −27.6° (cl. 24, CHCl$_3$). The synthesis yield was 89% and the optical yield was 81% (see Reference 2).

EXAMPLE 3

One gram (6.3 mmol) of t-butyl acetoacetate was asymmetrically reduced in accordance with the procedure described in Example 2. There was obtained 0.73 g of the t-butyl ester of R-(−)-hydroxybutanoic acid, having a specific rotation of $[\alpha]_D^{20}$ of −30.3° (cl. 70, CHCl$_3$ 13). The synthetic yield was 73% and the optical yield was 84% (see Reference 3).

EXAMPLE 4

One gram (6.2 mmol) of methyl phenylglyoxylate was asymmetrically reduced in accordance with the procedure described in Example 2. There was obtained 0.91 g of the methyl ester of R(−)-hydroxy-2-phenylacetic acid, having a specific rotation $[\alpha]_D^{20}$ of −103.3° (cl. 05, CHCl$_3$). The synthesis yield was 91% and the optical yield was 71% (see Reference 3).

EXAMPLE 5

One gram (8.6 mmol) of ethyl pyruvate was asymmetrically reduced in accordance with the procedure described in Example 2. There was obtained 0.36 g of the ethyl ester of R(+)-2-hydroxypropionic acid, having a specific rotation $[\alpha]_D^{20}$ of +7.3° (cl. 02, acetone). The synthesis yield was 35% and the optical yield was 74% (see Reference 4).

EXAMPLE 6

One gram (6.9 mmol) of the ethyl ester of 3-oxopentanoic acid was asymmetrically reduced in accordance with the procedure described in Example 2. There was obtained 0.82 g of the ethyl ester of R-(−)-3-hydroxypentanoic acid, having a specific rotation $[\alpha]_D^{20}$ of −25.9° (cl. 02, CHCl$_3$). The synthesis yield was 82% and the optical yield was 75% (see Reference 5).

EXAMPLE 7

One gram (6.9 mmol) of ethyl 4-chloroacetoacetate was asymmetrically reduced in accordance with the procedure described in Example 2. There was obtained 0.81 g of the ethyl ester of R(−)-4-hydroxybutanoic acid having a specific rotation $[\alpha]_D^{20}$ of −14.2° (cl. 79, CHCl$_3$). The synthesis yield was 80% and the optical yield was 65% (see Reference 6).

EXAMPLE 8

A solution of 2.33 g (15.5 mmol) of L-(+)-tartaric acid in 50 ml of tetrahydrofuran (THF) was cooled in a cryostat at −20° C., and a solution of 0.5 g (3.8 mmol) of ethyl acetoacetate in THF (2 ml) was added. To the resulting solution, there was further added 0.59 g (15.5 mmol) of sodium borohydride, all at one and with stirring, and the mixture was stirred for 13 hours. The reaction mixture was cooled in an ice bath, 25 ml of 1N HCl was added, and stirring was continued for 30 minutes. After distilling off THF under reduced pressure, the aqueous layer was extracted twice with ether (50 ml and 30 ml), and the combined extract was washed first with 30 ml of a saturated aqueous solution of sodium bicarbonate and then with 30 ml of a saturated aqueous solution of sodium chloride, and then dried over anhydrous magnesium sulfate. The solvent was distilled off under reduced pressure from the dried solution, and the residue was purified by silica gel column chromatography, giving 0.30 g ethyl (R)-(−)3-hydroxybutanoate as a fraction of ethyl acetate:n-hexane (1:5). Its specific rotation $[\alpha]_D^{22}$ was −34.1° (cl. 20, CHCl$_3$). The synthesis yield was 59% and the optical yield was 79% e.e. (see Reference 2).

EXAMPLE 9

A solution of 1.70 g (11.3 mmol) of L-(+)-tartaric acid in 35 ml of THF was cooled in a cryostat at −20° C., and a solution of 0.5 g (2.8 mmol) of ethyl phenylglyoxylate in THF (5 ml) was added. To the resulting solution, there was further added 0.43 g (11.3 mmol) of sodium borohyride, all at once and with stirring, and the mixture was stirred for 24 hours. The reaction mixture was cooled in an ice bath, 20 ml of 1N HCl was added, and stirring was continued for 15 minutes. After distilling off THF under reduced pressure, the aqueous layer was extracted twice with ethyl acetate (30 ml and 20 ml), and the combined extract was washed first with 20 ml of a saturated aqueous solution of sodium chloride, and then dried over anhydrous magnesium sulfate. The solvent was distilled off under reduced pressure from the dried solution, and the residue was purified by silica gel column chromatography, giving 0.43 g of ethyl (R)-(−)-2-hydroxy-2-phenylacetate as an ethyl acetate:n-hexane fraction(1:5). Its specific rotation $[\alpha]_D^{16}$ was −108.4° (cl. 12, CHCl$_3$). The synthesis yield was 85% and the optical yield was 85% e.e (see Reference 7).

EXAMPLE 10

To a dispersion of 0.43 g (11.3 mmol) of sodium borohydride in THF (35 ml), there was added 1.70 g (11.3 mmol) of L-(+)-tartaric acid, and the mixture was heated under reflux for four hours in an oil bath at 70° C. with stirring. The resulting mixture was cooled in a cryostat at −20° C., a solution of 0.5 g (2.8 mmol) of ethyl phenylglyoxylate in THF (5 ml) was added dropwise over a period of ten minutes, and stirring was continued for 19 hours. The reaction mixture was treated in the same manner as in Example 6, giving 0.44 of ethyl (R)-(−)-2-hydroxy-2-phenylacetate, having a specific rotation $[\alpha]_D^{16}$ of −109° (cl. 00, CHCl$_3$).

EXAMPLE 11

Ethyl 2,2-dimethylacetoacetate (0.5 g, 3.1 mmol) was asymmetrical reduced in accordance with the procedure described in Example 2, giving 0.34 g of ethyl 2,2-dimethyl-3-hydroxybutanoate. The product was converted to an ester of (R)-(+)-α-methoxy-α-trifluoromethylphenylacetic acid by a known technique (MTPA method, as described in Reference 8), and the optical yield was determined from its $^1$HNMR data. The synthesis yield was 60% e.e.

EXAMPLE 12

Ketopantolactone (0.5 g, 3.9 mmol) was asymmetrical reduced, with cooling in an ice-water bath, in accordance with the procedure described in Example 2, giving 0.33 g of (R)-(−)-pantolactone, having a specific rotation $[\alpha]_D^{21}$ of −19.0° (cl. 19, H$_2$O). The synthesis yield was 65% and the optical yield was 37% e.e. (see Reference 9).

EXAMPLE 13

Acetoacetanilide (1.0 g, 5.6 mmol) was asymmetrically reduced in accordance with the procedure described in Example 2, giving 0.7 g of (−)-3-hydroxybutanoic acid anilide, having a specific rotation $[\alpha]_D^{21}$ of −14.2° (cl. 03, acetone). The synthesis yield was 83% and the optical yield was 65% e.e. (see Reference 10).

EXAMPLE 14

Phenylglyoxylic acid benzylamide (1.0 g, 4.1 mmol) was asymmetrically reduced, with cooling in an ice-water bath, in accordance with the procedure described in Example 2, giving 1.04 g of (R)-(−)-N-benzylmandelamide, having a specific rotation $[\alpha]_C^{21}$ of −54.5° (cl. 04, $CHCl_3$) The synthesis yield was 100% and the optical yield was 68% e.e (see Reference 11).

EXAMPLE 15

To a dispersion of 1.0 g (26.3 mmol) of sodium borohydride in THF (80 ml), there was added 3.95 g (26.3 mmol) of L-(+)-tartaric acid, and the mixture was heated under reflux for four hours in an oil bath at 70° C. with stirring. The resulting mixture was cooled in a cryostat at −20° C., a solution of 1.0 g (6.6 mmol) of phenylglyoxylic acid in THF (5 ml) was added dropwise with stirring over a period of ten minutes, and stirring was continued for 67 hours. The reaction mixture was cooled in an ice bath, 30 ml of 1N HCl was added, and stirring was further continued for 30 minutes. After distilling off the solvent under reduced pressure, the residue was extracted twice with 20 ml ether, and the combined extract was washed with 50 ml of a saturated aqueous solution of sodium chloride and then dried over anhydrous magnesium sulfate. The dried solution was concentrated to about 30 ml, and an ethereal solution of diazomethane was added to the concentrate to esterify the reaction product. After distilling off the solvent under reduced pressure, the residue was purified by silica gel column chromatography, giving 1.03 g of methyl (R)-(−)-2-hydroxy-2-phenylacetate as a fraction in ethyl acetate:n-hexane (1:5). Its specific rotation $[\alpha]_D^{21}$ was −100.0° (cl. 09, MeOH). The synthesis yield was 93% and the optical yield was 65% e.e. (see Reference 3).

EXAMPLE 16

2-Chloroacetophenone (1.0 g, 6.4 mmol) was asymmetrically reduced, with cooling, in an ice-water bath, in accordance with the procedure described in Example 2, giving 0.82 g of (R)-(+)-2-chloro-1-phenylethyl alcohol, having a specific rotation $[\alpha]_D^{20}$ of +9.3° (cl. 39, cyclohexane). The synthesis yield was 82% and the optical yield was 19% e.e. (see Reference 12).

EXAMPLE 17

2-Hydroxyacetophenone (1.0 g, 7.3 mmol) was asymmetrically reduced, with cooling in an ice-water bath in accordance with the procedure described in Example 2, giving 0.8 g of (R)-(−)-phenyl-1,2-ethanediol, having a specific rotation $[\alpha]_D^{21}$ of −22.1° (cl. 02, acetone). The synthesis yield was 80% and the optical yield was 48% e.e (see Reference 13).

EXAMPLE 18

2-Methoxyacetophenone (0.5 g, 3.3 mmol) was asymmetrically reduced, with cooling in an ice-water bath, in accordance with the procedure described in Example 11, giving 0.44 g of 2-methoxy-1-phenylethyl alcohol. The synthesis yield was 87% and the optical yield was 84% e.e.

EXAMPLE 19

A dispersion of 0.43 g (11.3 mmol) of sodium borohydride in THF (20 ml) was cooled in a cryostat at −20° C., 1.38 g (11.3 mmol) of benzoic acid was added with stirring, and the mixture was stirred for two to three minutes. A solution of diethyl L-(+)-tartrate in THF (10 ml) was then added, the mixture was stirred for five minutes, a solution of 5 g (2.8 mmol) of ethyl phenylglyoxylate in THF (2 ml) was further added over a period of one to two minutes, and stirring was continued for one hour. The reaction mixgture was treated in the same manner as described in Example 1, giving 0.43 g of ethyl (S)-(+)-2-hydroxy-2-phenylacetate, having specific rotation $[\alpha]_D^{18}$ of +17.6° (cl. 18, $CHCl_3$). The synthesis yield was 85% and the optical yield was 15% e.e. (see Reference 7).

EXAMPLE 20

Ethyl phenylglyoxylate acid (0.5 g) was asymmetrically reduced in the same manner as in Example 19, except that 1.33 g (11.2 mmol) of succinic acid was used in place of benzoic acid, giving 0.44 g of ethyl (S)-(+)-2-hydroxy-2-phenylacetate, having a specific rotation $[\alpha]_D^{18}$ of +19.4° (cl. 18, $CHCl_3$). The synthesis yield was 87% and the optical yield was 15% e.e. (see Reference 7).

EXAMPLE 21

Ethyl phenylglyoxylate (1.6 mmol) was asymmetrically reduced in the same manner as in Example 6, except that DMF was used as the reaction medium, giving 0.25 g of ethyl (R)-(−)-2-hydroxy-2-phenylacetate, having specific rotation $[\alpha]_D^{20}$ of 38.8° (cl. 00, $CHCl_3$). The synthesis yield was 80% and the optical yield was 75% e.e.

The references referred to in the Examples are as follows:

Reference 1 : D. Seebach, F. Giovannini and B. Lamatsch, *Helv. Chim. Acta.*, 68, 958 (1985)

Reference 2 : D. Seebach and M Züger, *Helv. Chim. Acta.*, 65, 495 (1982)

Reference 3 : "Aldrich Catalog Handbook of Fine Chemicals," Aldrich Chemical Co., Inc., Milwaukee, 1984

Reference 4 : B. S. Deol, D. D. Ridley and G. W. Simpson, *Aust. J. Chem.*, 29., 2459 (1976)

Reference 5 : D. Seebach and M. F. Züger, *Tetrahedron Lett.*, 25, 2747 (1984)

Reference 6 : R. Pellegata, I. Dosi, M. Villa, G. Lesma and G. Palmisano, *Tetrahedron*, 41, 5607 (1985)

Reference 7 : P. Walden, *Z. Phys. Chem.*, 17, 705 (1895)

Reference 8 : J. A. Dale, D. L. Dull, and H. S. Mosher, *J Org. Chem.*, 34, 2543 (1969)

Reference 9 : E. T. Stiller, S. A. Harris, J. A. Harris, J. Finkelstein, J. C. Keresztesy, and K. Folkers, *J. Am. Chem. Soc.*, 62, 1785 (1940).

Reference 10 : B. S. Deol, D. D. Rideley, and G. W. Simpson, *Aust. J. Chem.*, 29, 2459(1976). Tani, T. Ise, Y. Tatsuno, and T.

Reference 11 : K. Tani, T. Ise, Y. Tatsuno, and T. Saito, *J. Chem. Soc., Chem. Commun.*, 1984, 1641.

Reference 12 : J. W. Hartgerink, L. C. J. van der Lann, J. B. F. N. Engberts, and Th. J. de Boer, *Tetrahedron*, 27, 4323 (1971).

Reference 13 : Tomimori, and T. Oriyama, *Chem. Lett.*, 1985, 1359.

We claim:

1. A process for asymmetrically reducing a ketone containing a heteroatom or atoms on at least one of the α- and β-carbon atoms of at least one of the two groups attached to the carbonyl group of the ketone, which comprises reducing the ketone by the use of a reducing agent comprising (i) an optically active tartaric acid or ester thereof and (ii) a metal borohydride, thereby producing an optically active alcohol.

2. A process according to claim 1, wherein the hetero atom is an atom selected from the group consisting of nitrogen, oxygen, sulfur and halogen atoms.

3. A process according to claim 1, wherein the carbonyl compound is a ketoester, the process thereby producing an optical active hydroxyester.

4. A process according to claim 3, wherein the ketoester is a linear or cyclic ketoester represented by Formula I:

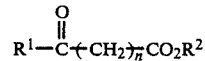 [I]

in which $R^1$ and $R^2$, which are the same or different, each represents an alkyl, an alkenyl, an alkynyl, an aryl or an aralkyl group which may contain one or more halogen atoms, or $R^1$ and $R^2$, individually or in combination, form a closed ring; and n represents an integer of 1 to 3.

5. A process according to claim 1, wherein the reduction is carried out at a temperature of from $-80°$ to $50°$ C.

6. A process according to claim 1, wherein the reduction is carried out in a medium selected from the group consisting of aromatic solvents and ethereal solvents.

7. A process according to claim 1, wherein the reducing agent comprises a reaction product of (i) the optical active tartaric acid or ester thereof and (ii) the metal borohydride.

8. A process according to claim 1, wherein the metal borohydride is sodium borohydride.

9. A process according to claim 1, wherein the metal borohydride is in the form of a metal borohydride-containing compound (i.e. a reaction product of (i) the optically active tartaric acid or the ester thereof and (ii) the metal borohydride).

* * * * *